US008636978B2

(12) United States Patent
Wood et al.

(10) Patent No.: US 8,636,978 B2
(45) Date of Patent: Jan. 28, 2014

(54) CYCLIZED NGR PEPTIDE COMPOUNDS, COMPOSITIONS, AND METHODS OF THEIR USE

(75) Inventors: Bradford J. Wood, Potomac, MD (US); Matthew Dreher, Rockville, MD (US); Ayele H. Negussie, Washington, DC (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 372 days.

(21) Appl. No.: 13/000,543

(22) PCT Filed: Jun. 15, 2009

(86) PCT No.: PCT/US2009/047328
§ 371 (c)(1),
(2), (4) Date: Apr. 4, 2011

(87) PCT Pub. No.: WO2010/005693
PCT Pub. Date: Jan. 14, 2010

(65) Prior Publication Data
US 2011/0200528 A1    Aug. 18, 2011

Related U.S. Application Data

(60) Provisional application No. 61/074,864, filed on Jun. 23, 2008, provisional application No. 61/106,722, filed on Oct. 20, 2008.

(51) Int. Cl.
*A61K 51/00* (2006.01)
*A61M 36/14* (2006.01)

(52) U.S. Cl.
USPC ......... 424/1.69; 424/1.11; 424/1.65; 424/9.1; 424/9.6; 514/1.1

(58) Field of Classification Search
USPC ........... 424/1.11, 1.65, 1.69, 1.81, 1.85, 1.89, 424/9.1, 9.2, 9.3, 9.4, 9.5, 9.6, 9.7, 9.8; 514/1, 1.1; 530/300, 317, 321, 323, 530/329, 330, 331
See application file for complete search history.

(56) References Cited

U.S. PATENT DOCUMENTS

| 4,415,732 | A |  | 11/1983 | Caruthers et al. |
| 4,458,066 | A |  | 7/1984 | Caruthers et al. |
| 4,500,707 | A |  | 2/1985 | Caruthers et al. |
| 4,668,777 | A |  | 5/1987 | Caruthers et al. |
| 4,725,677 | A |  | 2/1988 | Koster et al. |
| 4,973,679 | A |  | 11/1990 | Caruthers et al. |
| 5,132,418 | A |  | 7/1992 | Caruthers et al. |
| RE34,069 | E |  | 9/1992 | Koster et al. |
| 6,200,598 | B1 | * | 3/2001 | Needham ................. 424/450 |
| 6,726,925 | B1 | * | 4/2004 | Needham ................. 424/450 |

FOREIGN PATENT DOCUMENTS

| WO | WO 90/02749 A1 | 3/1990 |
| WO | WO 2004/031218 A1 | 4/2004 |
| WO | WO 2006/067633 A2 | 6/2006 |

OTHER PUBLICATIONS

Alul Rh, et al., Oxalyl-CPG: a labile support for synthesis of sensitive oligonucleotide derivatives. Nucleic Acids Res. Apr. 11, 1991;19(7):1527-32.
Atherton, et al., Letter: Polyamide supports for polypeptide Synthesis J. Am. Chem. Soc., 1975, 97, 6584.
Atherton, et al., Peptide synthesis. Part 2. Procedures for solid-phase synthesis using $N^\alpha$-fluorenylmethoxycarbonylamino-acids on polyamide supports. Synthesis of substance P and of acyl carrier protein 65-74 decapeptide. J. C. S. Perkin 1 538-546 (1981).
Atherton, et al., The polyamide method of solid phase peptide and oligonucleotide synthesis. Bioorg. Chem. 1979, 8, 351-370.
Bayer and Jung, A new support for polypeptide synthesis in columns. Tetrahedron Lett., 1970, 4503.
Berg, et al., Long-chain polystyrene-grafted polyethylene film matrix: a new support for solid-phase peptide synthesis. J. Am. Chem. Soc., 1989, 111, 8024.
Bonora et al., A Liquid-Phase Process Suitable for Large-Scale Synthesis of Phosphorothioate Oligonucleotides. Organic Process Research & Development, 2000, 4, 225-231.
Colombo, et al., Structure-activity relationships of linear and cyclic peptides containing the NGR t umor-homing motif. J. Biol. Chem., 277(49), 47891-47897 (Dec. 2002).
Curnis, et al., Differential binding of drugs containing the NGR motif to CD13 isoforms in tumor vessels, epithelia, and myeloid cells. Cancer Res. 62, 867 (2002).
Curnis, et al., Improving chemotherapeutic drug penetration in tumors by vascular targeting and barrier alteration. J. Clin. Invest. 110, 475-82(2002).
Daniels, et al.,Membranes as solid supports for peptide synthesis. Tetrahedron Lett. 1989, 4345-4348.

(Continued)

*Primary Examiner* — D L Jones
(74) *Attorney, Agent, or Firm* — Woodcock Washburn LLP (57) ABSTRACT

Cyclized peptide compounds containing the NGR motif of formula (I) or a pharmaceutically-acceptable salt thereof are disclosed. Compositions comprising the cyclized peptide compounds and methods of their use are also disclosed.

36 Claims, 7 Drawing Sheets (56) References Cited

OTHER PUBLICATIONS

Eichler, et al., Application of cellulose paper as support material in simultaneous solid phase peptide synthesis. Collect. Czech. Chem. Commun., 1989, 54, 1746-1752.
Folkman, Role of angiogenesis in tumor growth and metastasis. Semin. Oncol. 29, (6 Suppl 16) 15-18 (2002).
Garde, et al., Binding and internalization of NGR-peptide-targeted liposomal doxorubicin (TVT-DOX) in CD13-expressing cells and its antitumor effects. Anti-Cancer Drugs, 18, 1189-1200 (2007).
Geysen HM, et al., Use of peptide synthesis to probe viral antigens for epitopes to a resolution of a single amino acid. Proc Natl Acad Sci U S A. Jul. 1984;81(13):3998-4002.
Gorman, An apparatus for simultaneous manual solid-phase synthesis of multiple peptide analogs. Anal. Biochem., 1984, 136, 397.
Greene and Wuts, Protective Groups in Organic Synthesis, Chapter 7, 2d ed, John Wiley & Sons, New York, 1991.
Holm and Meldal, in "Proceedings of the 20th European Peptide Symposium", G. Jung and E. Bayer, eds., Walter de Gruyter & Co., Berlin, 1989 pp. 208-210.
Houghten RA. General method for the rapid solid-phase synthesis of large numbers of peptides: specificity of antigen-antibody interaction at the level of individual amino acids. Proc Natl Acad Sci U S A. Aug. 1985;82(15):5131-5.
Jain, Molecular regulation of vessel maturation. Nat. Med. 9:685-693 (Jun. 2003).
Kent and Merrifield, Israel J. Chem. 1978, 17, 243.
Krchnak, et al., Multiple continuous-flow solid-phase peptide synthesis. Synthesis of an HIV antigenic peptide and its omission analogues. Int. J. Peptide Protein Res., Mar. 1989, 33, 209.
Lebl and Eichler, Simulation of continuous solid phase synthesis: synthesis of methionine enkephalin and its analogs. Peptide Res. Jul.-Aug. 1989, 2, 297-300.
Matter, Tumor angiogenesis as a therapeutic target. Drug Discov. Today, 6, 1005-1024 (Oct. 2001).
Parr and Grohmann, Solid-Phase Peptide Synthesis on an Inorganic Matrix having Organic Groups on the Surface. Angew. Chem. Internal. Ed. 1972, 11, 314-315.
Scott, et al., The Use of Resin Coated Glass Beads in the Form of a Packed Bed for the Solid Phase Synthesis of Peptides. J. Chrom. Sci., 1971, 9, 577-591.
Thorpe, et al., The first international conference on vascular targeting: meeting overview Cancer Res. 63, 1144-1147 (Mar. 2003).
Tregear, Chemistry and Biology of Peptides, J. Meienhofer, ed., Ann Arbor Sci. Publ., Ann Arbor, 1972 pp. 175-178.
van Rietschoten in Peptides 1974, Y. Wolman, Ed., Wiley and Sons, New York, 1975, pp. 113-116.
Wright, et al., Large scale synthesis of oligonucleotides via phosphoramidite nucleosides and a high-loaded polystyrene support. Tetrahedron Letters 1993, 34(21), 3373-3376.

* cited by examiner

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Lys or modified Lys where C substituted
      w/(CH2)4NR12R14, where R12 = H or C1-6 alkyl; R14 = H, C1-6 alkyl,
      amino protecting group, or diagnostic moiety; N substituted w/H or
      C1-6 alkyl
<220> FEATURE:
<221> NAME/KEY: MISC_FEATURE
<222> LOCATION: (2)..(2)
<223> OTHER INFORMATION: Asn or modified Asn where C substituted
      w/CH2C(=O)NR12R15, where R12 = H or C1-6 alkyl; R15 = H, C1-6
      alkyl, or amino protecting group; N substituted w/H or C1-6 alkyl
<220> FEATURE:
<221> NAME/KEY: MISC_FEATURE
<222> LOCATION: (3)..(3)
<223> OTHER INFORMATION: Gly or modifyed Gly where C substituted w/H or
      C1-6 alkyl; N substituted w/H or C1-6 alkyl
<220> FEATURE:
<221> NAME/KEY: MISC_FEATURE
<222> LOCATION: (4)..(4)
<223> OTHER INFORMATION: Arg or modified Arg where C substituted
      w/(CH2)3NHC(R12R14) (=N+R12R1, where R12=H or C1-6 alkyl; R14=H,
      C1-6 alkyl, amino protecting group, or diagnostic moiety; R16=H,
      C1-6 alkyl, or guanidino-protecting group; N substituted w/H or
      C1-6 alkyl
<220> FEATURE:
<221> NAME/KEY: MISC_FEATURE
<222> LOCATION: (5)..(5)
<223> OTHER INFORMATION: Glu or modified Glu where both backbone C
      substituted w/H or C1-6 alkyl; N substituted w/H or C1-6 alkyl

<400> SEQUENCE: 1

Lys Asn Gly Arg Glu
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Lys is labeled with Oregon Green dye
<220> FEATURE:
<221> NAME/KEY: MISC_FEATURE
<222> LOCATION: (5)..(5)
<223> OTHER INFORMATION: Linkage to make cyclic is between Lys and Glu

<400> SEQUENCE: 2
```

```
Lys Asn Gly Arg Glu
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Linkage to make cyclic is between Lys and Glu

<400> SEQUENCE: 3

Lys Asn Gly Arg Glu
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic construct

<400> SEQUENCE: 4

Lys Asn Gly Arg Glu
1               5
```

CYCLIZED NGR PEPTIDE COMPOUNDS, COMPOSITIONS, AND METHODS OF THEIR USE

CROSS-REFERENCE TO RELATED APPLICATIONS

This application is the national stage of PCT/US2009/047328, filed Jun. 15, 2009, which claims the benefit of priority to U.S. Provisional Application No. 61/074,864, filed Jun. 23, 2008, and U.S. Provisional Application No. 61/106,722 filed Oct. 20, 2008, the disclosures of which are incorporated herein by reference in their entireties.

STATEMENT OF FEDERALLY SPONSORED RESEARCH

The U.S. Government may have certain rights in the invention described herein, which was made in part with funds from NIH Contract No. HHSN263200700019I.

FIELD OF THE INVENTION

The present invention relates to peptides useful in targeting therapeutic and diagnostic agents to cancer cells. More specifically, the present relates to NGR peptides for targeting cancer cells, especially tumors expressing aminopeptidase N isoform CD13.

BACKGROUND OF THE INVENTION

Traditional approaches to cancer therapies have focused on targeting and destroying cancer cells. However, direct access to the cancer cells is often limited. More recent strategies have focused on targeting tumor vasculature, rather than the cancer cells directly, to suppress the formation of new blood vessels and/or to destroy established tumor vasculature, and eventually starve the tumor and send it into regression [Matter, *Drug Discov. Today*, 6, 1005-1024 (2001); Thorpe, et al., *Cancer Res.* 63, 1144-1147 (2003); Folkman, *Semin. Oncol.* 29, 15-18 (2002); Garde, et al., *Anti-Cancer Drugs*, 18, 1189-1200 (2007)].

Tumor vasculature has an abnormal wall structure and the endothelial cells in the angiogenic vessels within solid tumors express several proteins that are present in very low quantities or totally absent in established blood vessels, including aminopeptidase N isoform CD13 (APN/CD13). Jain, *Nat. Med.* 9:685-693 (2003).

The NGR (Asn-Gly-Arg) peptide motif is a ligand for APN/CD13. This peptide motif homes inside tumors, offering a means to target therapeutic and diagnostic agents into solid tumors by linking the therapeutic or diagnostic agent to the NGR peptide. NGR-containing peptides have been proven useful for delivering cytotoxic drugs, apoptotic peptides, and cytokines [such as tumor necrosis factor (TNF)] to tumor vasculature. Curnis, et al., *Cancer Res.* 62, 867 (2002); Curnis, et al., *J. Clin. Invest.* 110, 475 (2002).

Both linear and disulfide-bridged cyclic peptides containing the NGR motif have been used to deliver various anti-tumor compounds and viral particles to tumor vessels, with the cyclic versions showing more than a 10 fold higher anti-tumor activity than their linear counterparts. Colombo, et al., *J. Biol. Chem.*, 277(49), 47891-47897 (2002).

The disulfide-bridged cyclic peptides containing the NGR motif are not stable and breakdown under certain physiological conditions in cellular environments. Accordingly, there is a pressing need to permanently cyclized compounds having the NGR peptide motif to target APN/CD13. The invention is directed to these, as well as other, important needs.

SUMMARY OF THE INVENTION

In one aspect, the present invention is directed to compounds of formula I (SEQ ID NO:1):

or a pharmaceutically-acceptable salt thereof;
wherein:
$R^1$ is $(CH_2)_4NR^{12}R^{14}$;
$R^2$ is hydrogen or $C_1$-$C_6$alkyl;
$R^3$ is $CH_2C(=O)NR^{12}R^{15}$;
$R^4$ is hydrogen or $C_1$-$C_6$alkyl;
$R^5$ is hydrogen or $C_1$-$C_6$alkyl;
$R^6$ is hydrogen or $C_1$-$C_6$alkyl;
$R^7$ is $(CH_2)_3NHC(NR^{12}R^{14})(=N^+R^{12}R^{16})$;
$R^8$ is hydrogen or $C_1$-$C_6$alkyl;
$R^9$ is hydrogen or $C_1$-$C_6$alkyl;
$R^{10}$ is hydrogen or $C_1$-$C_6$alkyl;
$R^{11}$ is hydrogen or $C_1$-$C_6$alkyl;
each $R^{12}$ is, independently, hydrogen or $C_1$-$C_6$alkyl;
$R^{13}$ is hydrogen, $C_1$-$C_6$alkyl, or -(L)$_n$-sm;
  L is a linking moiety;
  n is 0 or 1;
  sm is a support medium;
$R^{14}$ is hydrogen, $C_1$-$C_6$alkyl, amino protecting group, or a diagnostic moiety;
$R^{15}$ is hydrogen, $C_1$-$C_6$alkyl, or amino protecting group; and
$R^{16}$ is hydrogen, $C_1$-$C_6$alkyl, or a guanidino-protecting group.

In another aspect, the present invention is directed to compositions, comprising:
  a compound of formula I or a pharmaceutically acceptable salt thereof;
  a lipid-bilayer;
  at least one therapeutic or diagnostic agent; and
  optional polyethylene glycol.

In other aspects, the present invention is directed to methods of selectively targeting cancerous tissue in a patient in need thereof, comprising the step of:
  administering to said patient the composition described herein;
  wherein said cancerous tissue, including tumor vasculature, expresses aminopeptidase N isoform CD13 (APN/CD13).

The foregoing general description and the following detailed description are exemplary and explanatory only and are not restrictive of the invention, as defined in the appended claims.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings:

FIG. 1 shows a synthetic scheme for producing compounds of formula I where (a) N-protected-Glu-OAll-OH (or suitable $R^9$, $R^{10}$ substituted version thereof) (2.5 equivalents), HATU (2 equivalents), DIPEA (4 equivalents), NMP, for example at room temperature for 30 minutes; (b) piperidine-DMF (1:4), for example, at room temperature for 5 minutes (×2); (c) N-protected-Arg-Pbf-OH (or suitable $R^6$, $R^7$ substituted version thereof) (2 equivalents), HATU (2 equivalents), DIPEA (4 equivalents), for example at room temperature for 30 minutes; (d) N-protected-Gly-OH, HATU (or suitable $R^4$, $R^5$ substituted version thereof) (2 equivalents), DIPEA (4 equivalents), for example at room temperature for 30 minutes; (e) N-protected-Asn-Trt-OH, HATU (or suitable $R^2$, $R^3$ substituted version thereof) (2 equivalents), DIPEA (4 equivalents), for example at room temperature for 30 minutes; (f) N-Fmoc-Lys-Boc-OH (or suitable $R^1$, $R^{11}$ substituted version thereof), HATU (2 equivalents), DIPEA (4 equivalents), for example at room temperature for 30 minutes; (g) catalyst such as $Pd(PPh_3)_4$ (2 equivalents), $CHCl_3$—AcOH—N-methylmorpholine (37:2:1), for example, at room temperature for 2 hours; (h) HATU (2 equivalents), DIPEA (4 equivalents), for example, at room temperature for 17 hours; (i) TFA-$CH_2Cl_2$ (1:1), for example, at room temperature for 2 hours.

FIG. 2 shows a synthetic scheme for producing the compound of EXAMPLE 1 where (a) N-protected-Glu-OAll-OH (2.5 equivalents), HATU (2 equivalents), DIPEA (4 equivalents), NMP, for example at room temperature for 30 minutes; (b) piperidine-DMF (1:4), for example, at room temperature for 5 minutes (×2); (c) N-protected-Arg-Pbf-OH (2 equivalents), HATU (2 equivalents), DIPEA (4 equivalents), for example at room temperature for 30 minutes; (d) N-protected-Gly-OH, HATU (2 equivalents), DIPEA (4 equivalents), for example at room temperature for 30 minutes; (e) N-protected-Asn-Trt-OH, HATU (2 equivalents), DIPEA (4 equivalents), for example at room temperature for 30 minutes; (f) N-Fmoc-Lys-Boc-OH, HATU (2 equivalents), DIPEA (4 equivalents), for example at room temperature for 30 minutes; (g) catalyst such as $Pd(PPh_3)_4$ (2 equivalents), $CHCl_3$—AcOH—N-methylmorpholine (37:2:1), for example, at room temperature for 2 hours; (h) HATU (2 equivalents), DIPEA (4 equivalents), for example, at room temperature for 17 hours; (i) TFA-$CH_2Cl_2$ (1:1), for example, at room temperature for 2 hours.

FIGS. 5A to 5F show fluorescence micrographs of in vitro binding of anti-CD13 antibody (FIGS. 5A, 5B, and 5C) and cK(OG)NGRE (SEQ ID NO:2) (FIGS. 5D, E, and F) to CD13-positive HT-1080 cells (FIGS. 5B, C, E, and F) and CD13-negative MCF7 cells (FIGS. 5A and D), where:

green is a signal from cK(OG)NGRE (SEQ ID NO:2) or anti-CD13 antibody; and blue is signal from the nuclear staining agent DAPI.

Bar equals 100 µM for FIGS. 5A, B, D, and E and 50 µM for FIGS. 5C and F.

DETAILED DESCRIPTION OF ILLUSTRATIVE EMBODIMENTS

As used herein and in the appended claims, the singular forms "a," "an," and "the" include the plural reference unless the context clearly indicates otherwise. Thus, for example, a reference to "a compound" is a reference to one or more compounds and equivalents thereof known to those skilled in the art, and so forth.

The term "alkyl," as used herein, refers to an aliphatic hydrocarbon chain, the hydrocarbon chain can have up to 20 carbon atoms, and preferably 1 to 6 carbon atoms, and more preferably 1 to 4 carbon atoms. The term "alkyl" includes, but is not limited to, straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. In some embodiments, the alkyl group is preferably branched having 3 to 6 carbon atoms. The term "straight chain alkyl" refers to an unbranched alkyl group. The term "lower alkyl" refers to an alkyl group having 1 to 4 carbon atoms.

The phrase "linking group," as used herein, refers to a physiologically-compatible chemical group that links the functional domains of the compounds. In general, the linking group does not contribute significantly to the binding or image enhancing functionality of the diagnostic agent. In some cases, the presence of the linking group may be preferred based on synthetic considerations. In other cases, the linking group may facilitate operation of the bioactivity. Examples of the linking groups include linear, branched, or cyclic alkyl, aryl, ether, polyhydroxyl, polyether, polyamine, heterocyclic, peptide, peptoid, or other physiologically compatible covalent linkages.

The phrase "support medium," as used herein, refers to all forms of support known to the art skilled for the synthesis of peptides.

The phrase "protecting group," as used herein, refers to a chemical functional group that can be selectively appended to and removed from functionalities, such as amino groups, guanidino groups, hydroxyl groups, and carboxyl groups. These groups are present in a chemical compound to render such functionality inert to chemical reaction conditions to which the compound is exposed. Protecting groups that may be employed in accordance with the present invention may be described in Greene, T. W. and Wuts, P. G. M., *Protective Groups in Organic Synthesis* 2d. Ed., Wiley & Sons, 1991.

The phrase "diagnostic moiety," as used herein, refers to the residue of a chemical entity that may be used to detect, image and/or monitor the presence and/or progression of a condition(s), pathological disorder(s) or disease(s).

The abbreviation "DSPE-$PEG_{2000}$" is 1,2-distearoyl-sn-glycero-3-phosphoethanolamine-N—[PEG(2000)] useful in the preparation of liposomes and is available from Avanti Polar (Alabama, USA).

The phrase "solid tumors," as used herein, refers to those growing in an anatomical site other than the bloodstream (in contrast to blood-borne tumors such as leukemias). Solid tumors require the formation of small blood vessels and capillaries to nourish the growing tumor tissue.

In one embodiment, the invention is directed to compounds of formula I (SEQ ID NO:1):

I or a pharmaceutically-acceptable salt thereof;
wherein:
$R^1$ is $(CH_2)_4NR^{12}R^{14}$;
$R^2$ is hydrogen or $C_1$-$C_6$alkyl;
$R^3$ is $CH_2C(=O)NR^{12}R^{15}$;
$R^4$ is hydrogen or $C_1$-$C_6$alkyl;
$R^5$ is hydrogen or $C_1$-$C_6$alkyl;
$R^6$ is hydrogen or $C_1$-$C_6$alkyl;
$R^7$ is $(CH_2)_3NHC(NR^{12}R^{14})(=N^+R^{12}R^{16})$;
$R^8$ is hydrogen or $C_1$-$C_6$alkyl;
$R^9$ is hydrogen or $C_1$-$C_6$alkyl;
$R^{10}$ is hydrogen or $C_1$-$C_6$alkyl;
$R^{11}$ is hydrogen or $C_1$-$C_6$alkyl;
each $R^{12}$ is, independently, hydrogen or $C_1$-$C_6$alkyl;
$R^{13}$ is hydrogen, $C_1$-$C_6$alkyl, or -(L)$_n$-sm;
  L is a linking moiety;
  n is 0 or 1;
  sm is a support medium;
$R^{14}$ is hydrogen, $C_1$-$C_6$alkyl, amino protecting group, or a diagnostic moiety;
$R^{15}$ is hydrogen, $C_1$-$C_6$alkyl, or amino protecting group; and
$R^{16}$ is hydrogen, $C_1$-$C_6$alkyl, or a guanidino-protecting group.

In certain preferred embodiments of the compounds of formula I, $R^1$ is $(CH_2)_4NH_2$.
In certain preferred embodiments, $R^2$ is hydrogen.
In certain preferred embodiments, $R^3$ is $CH_2C(=O)NH_2$.
In certain preferred embodiments, $R^4$ is hydrogen.
In certain preferred embodiments of the compounds of formula I, $R^5$ is hydrogen.
In certain preferred embodiments of the compounds of formula I, $R^6$ is hydrogen.
In certain preferred embodiments of the compounds of formula I, $R^7$ is $(CH_2)_3NHC(NH_2)(=N^+H_2)$.
In certain preferred embodiments of the compounds of formula I, $R^8$ is hydrogen.
In certain preferred embodiments of the compounds of formula I, $R^9$ is hydrogen.

In certain preferred embodiments of the compounds of formula I, $R^{10}$ is hydrogen.
In certain preferred embodiments of the compounds of formula I, $R^{11}$ is hydrogen.
In certain preferred embodiments of the compounds of formula I, $R^{12}$ is hydrogen.
In certain preferred embodiments of the compounds of formula I, $R^{13}$ is hydrogen.
In certain preferred embodiments of the compounds of formula I, $R^{13}$ is -(L)$_n$-sm. In other especially preferred embodiments, L is Some representative support media that are amenable to the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., Organic Process Research & Development, 2000, 4, 225-231).

The support medium may be a controlled pore glass, oxalyl-controlled pore glass, silica-containing particles, polymers of polystyrene, copolymers of polystyrene, copolymers of styrene and divinylbenzene, copolymers of dimethylacrylamide and N,N'-bisacryloylethylenediamine, soluble support medium or PEPS.

Further support media amenable to the present invention include without limitation PEPS support a polyethylene (PE) film with pendant long-chain polystyrene (PS) grafts (molecular weight on the order of $10^6$, (see Berg, et al., J. Am. Chem. Soc., 1989, 111, 8024 and International Patent Application WO 90/02749),). The loading capacity of the film is as high as that of a beaded matrix with the additional flexibility to accommodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwell plates have not indicated any limitations of the synthetic efficacy.

Further support media amenable to the present invention include without limitation particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.*, 1975, 97, 6584, *Bioorg. Chem.* 1979, 8, 351, and J. C. S. Perkin 1538 (1981)).

Further support media amenable to the present invention include without limitation a composite of a resin and another material that is also substantially inert to the organic synthesis reaction conditions employed. One exemplary composite (see Scott, et al., *J. Chrom. Sci.*, 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243 and van Rietschoten in *Peptides* 1974, Y. Wolman, Ed., Wiley and Sons, New York, 1975, pp. 113-116). Contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis may be utilized. (Geysen, et al., *Proc. Natl. Acad. Sci. USA*, 1984, 81, 3998). A "tea bag" containing traditionally-used polymer beads. (Houghten, *Proc. Natl. Acad. Sci. USA*, 1985, 82, 5131). Simultaneous use of two different supports with different densities (Tregear, *Chemistry and Biology of Peptides*, J. Meienhofer, ed., Ann Arbor Sci. Publ., Ann Arbor, 1972 pp. 175-178). Combining of reaction vessels via a manifold (Gorman, *Anal. Biochem.*, 1984, 136, 397). Multicolumn solid-phase synthesis (e.g., Krchnak, et al., *Int. J. Peptide Protein Res.*, 1989, 33, 209), and Holm and Meldal, in "Proceedings of the 20th European Peptide Symposium", G. Jung and E. Bayer, eds., Walter de Gruyter & Co., Berlin, 1989 pp. 208-210). Cellulose paper (Eichler, et al., *Collect. Czech. Chem. Commun.*, 1989, 54, 1746). Support mediated synthesis of peptides have also been reported (see, *Synthetic Peptides: A User's Guide*, Gregory A. Grant, Ed. Oxford University Press 1992; U.S. Pat. No. 4,415,732; U.S. Pat. No. 4,458,066; U.S. Pat. No. 4,500,707; U.S. Pat. No. 4,668,777; U.S. Pat. No. 4,973,679; U.S. Pat. No. 5,132,418; U.S. Pat. No. 4,725,677 and Re 34,069.)

In certain preferred embodiments of the compounds of formula I, n is 0.

In certain preferred embodiments of the compounds of formula I, n is 1.

In certain preferred embodiments of the compounds of formula I, $R^{14}$ is hydrogen.

In other preferred embodiments of the compounds of formula I, $R^{14}$ is a diagnostic moiety. In certain embodiments of the invention, the diagnostic moiety is a fluorophore, non-metallic isotope, an optical reporter, a boron neutron absorber, a paramagnetic metal ion, a ferromagnetic metal, a gamma-emitting radioisotope, a positron-emitting radioisotope, or an x-ray absorber. In certain preferred embodiments, the diagnostic moiety is a fluorophore. One preferred fluorophore is In yet other preferred embodiments of the compounds of formula I, $R^{14}$ is an amino protecting group. A preferred amino protecting group with respect to $R^{14}$ is t-butyloxy carbonyl (BOC).

In other preferred embodiments of the compounds of formula I, $R^{15}$ is hydrogen.

In yet other preferred embodiments of the compounds of formula I, $R^{15}$ is an amino protecting group. A preferred amino protecting group with respect to $R^{15}$ is triphenylmethyl (trityl).

Representative amino protecting groups suitable for the purposes of this invention are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "amino acid" indicates that the molecular moiety contains one or more functionalities protected by protecting groups. Suitable amino protecting groups include, but are not limited to, methyl, formyl, ethyl, acetyl, t-butyl, anisyl, benzyl, trifluoroacetyl, N-hydroxysuccinimide, t-butyloxycarbonyl (Boc), benzoyl, 4-methylbenzyl, thioanizyl, thiocresyl, benzyloxymethyl, 4-nitrophenyl, benzyloxycarbonyl, 2-nitrobenzoyl, 2-nitrophenylsulphenyl, 4-toluenesulfonyl (tosyl), pentafluorophenyl, diphenylmethyl (Dpm), 2-chlorobenzyloxycarbonyl, 2,4,5-trichlorophenyl, 2-bromobenzyloxycarbonyl, 9-fluorenylmethyloxycarbonyl, triphenylmethyl (trityl; Trt), 2,2,5,7,8-pentamethyl-chroman-6-sulphonyl, Cbz, 2,3,6-trimethyl-4-methoxybenzenesulfonyl (Mtr), nitro, 5-sulfonyl-2,2,4,6,7-pentamethyl-benzofuran (Pbf), 2,2,5,7,8-pentamethylchroman-6-sulfonyl (Pmc), and adamantyloxycarbonyl. Preferred amino protecting groups include Pbf, Boc, and Trt.

Some amino acids are available, from Novabiochem, in their protected form, including, for example, Fmoc-Arg(Me, Pbf)-OH, Fmoc-ADMA(Pbf)-OH, and Fmoc-Lys(Me,Boc)-OH, where ADMA is asymmetric dimethylarginine. The Fmoc derivatives may be coupled using standard activation methods, and the Pbf group may be cleaved with standard TFA cleavage cocktails.

Fmoc-Arg(Me,Pbf)-OH

Fmoc-ADMA(Pbf)-OH

Fmoc-Lys(Me,Boc)-OH

In other preferred embodiments of the compounds of formula I, $R^{16}$ is hydrogen.

In yet other preferred embodiments of the compounds of formula I, $R^{16}$ is a guanidino-protecting group. A preferred guanidino-protecting group is 5-sulfonyl-2,2,4,6,7-pentamethyl-benzofuran (Pbf).

The compounds can be synthesized, for example, by the methods described herein, or variations thereon as appreciated by the skilled artisan. All methods disclosed in association with the present invention are contemplated to be practiced on any scale, including milligram, gram, multigram, kilogram, multikilogram or commercial industrial scale.

As will be readily understood, functional groups present may contain protecting groups during the course of synthesis.

Figure 1:
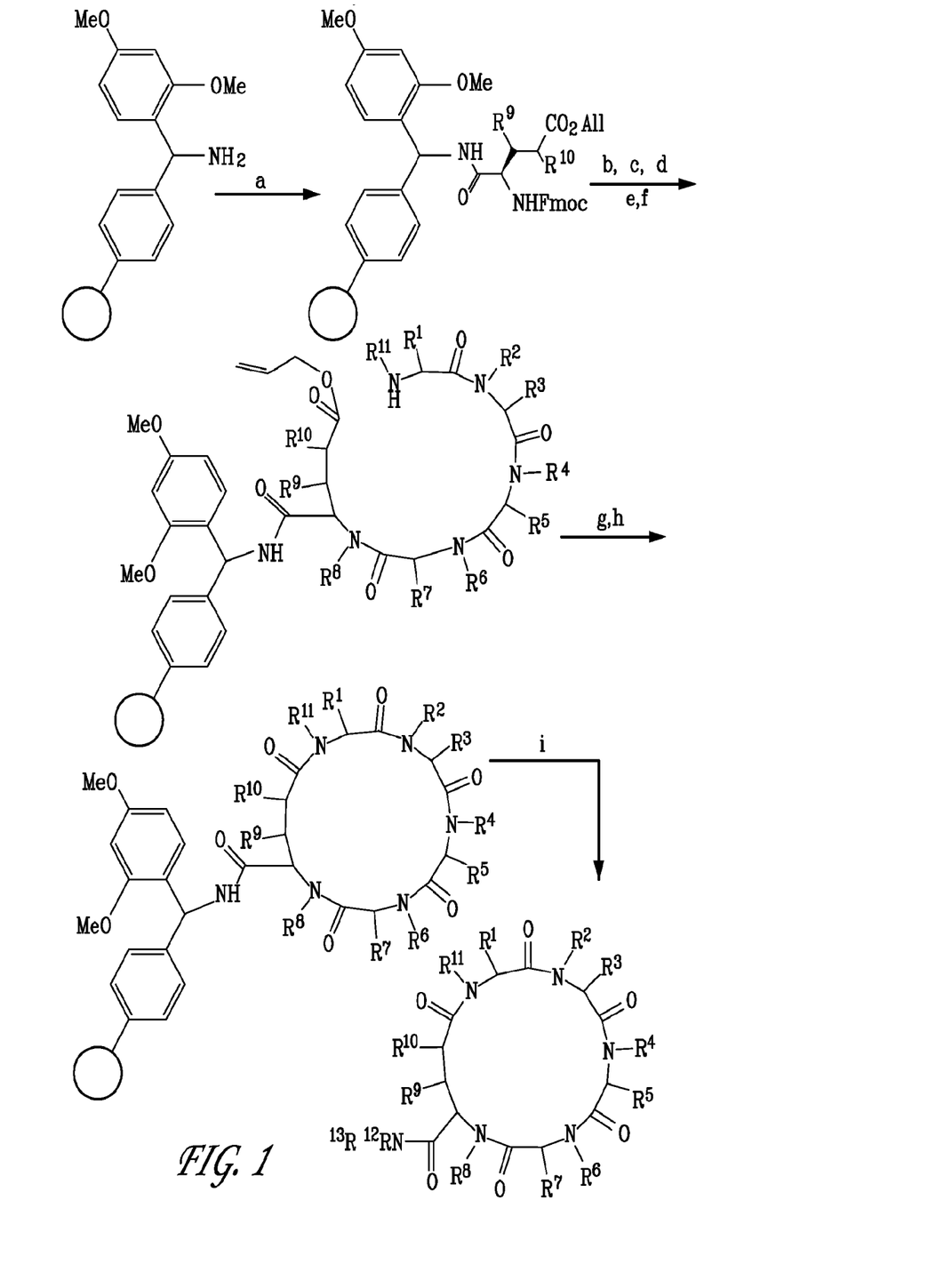

The compounds of formula I may be synthesized in accordance with FIG. 1, where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, L, n, and sm are as set forth herein.

In another embodiment, the invention is directed to compositions, comprising:
a compound of formula I or a pharmaceutically acceptable salt thereof;
a lipid-bilayer;
at least one therapeutic agent or diagnostic agent; and
optional polyethylene glycol.

While a preferred embodiment, the compositions comprising the compounds of formula I are not limited to this preferred embodiment.

In certain preferred embodiments, the lipid-bilayer comprises low temperature sensitive liposomes. Suitable liposomes are described in U.S. Pat. No. 6,200,598 and U.S. Pat. No. 6,726,925, which are incorporated herein by reference in their entirety.

The compounds of formula I may also be delivered with polymer and/or protein based drug delivery systems, including, but not limited to, simple polymers (such as HPMA), micelles, polymersomes, and the like.

In certain preferred embodiments, the therapeutic agent is an anti-tumor, anti-angiogenic, anti-neoplastic agent, or a combination thereof.

In certain preferred embodiments, the therapeutic agent is an anthracycline compound. Suitable anthracycline compound is daunorubicin, doxorubicin, epirubicin, idarubicin, mitoxantrone, a pharmaceutically-acceptable salt of daunorubicin, doxorubicin, epirubicin, idarubicin, or mitoxantrone, or a combination thereof. Doxorubicin is particularly preferred.

In certain preferred embodiments, wherein said compound of claim 1 or said pharmaceutically acceptable salt thereof is conjugated to said lipid bilayer.

In certain embodiments, the invention is directed to methods of selectively targeting cancerous tissue in a patient in need thereof, comprising the step of:
administering to said patient a composition described above;
wherein said cancerous tissue, including tumor vasculature, expresses aminopeptidase N isoform CD13 (APN/CD13).

The compositions of the present invention comprising the lipid bilayer, the compound of formula I, the active ingredient, and optional polyethylene glycol may be administered using methods that are known to those skilled in the art, including but not limited to delivery into the bloodstream of a subject or subcutaneous administration of the composition. For example, the composition may be administered intravenously and thereby brought to the site of a tumor by the normal blood flow.

In accordance with the present invention, the therapeutic agent, such as an anti-tumor or anti-neoplastic agent of choice, is entrapped within a liposome according to the present invention; the liposomes are formulated to be of a size known to penetrate the endothelial and basement membrane barriers. The resulting liposomal formulation can be administered parenterally to a subject in need of such treatment, preferably by intravenous administration. Tumors characterized by an acute increase in permeability of the vasculature in the region of tumor growth are particularly suited for treatment by the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods, and examples are illustrative only and not limiting.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Materials and Methods

NovaPEG Rink amide resin and all amino acids, except Fmoc-Arg(Pbf)-OH, were purchased from Novabiochem (California). Fmoc-Arg(Pbf)-OH was purchased from Chem-Impex International (Illinois). All solvents used for the synthesis were anhydrous and used as received. All other reagents were purchased from Sigma Aldrich. Solvents for HPLC were HPLC-grade. DSPE-PEG$_{2000}$CH$_2$COOH and Oregon Green were purchased from Avanti Polar Lipids, Inc. (Alabama) and Invitrogen, Corp. (California), respectively. $^1$H NMR and $^{13}$C NMR data were recorded on a Bruker Ultrashield 500 device at 300 MHz for proton and 75 MHz for carbon using D$_2$O. HETCOR and COSY-45 experiments were performed on a Mercury 300 MHz device from Varian. Mass spectral data were recorded on a PE/SCIEX API 2000 and MALDI-TOF mass spectrometer instrument.

Cell Culture:

Human fibrosarcoma (HT-1080) and human adenocarcinoma (MCF7) cells were purchased from American Type Culture Collection (ATCC, Manassas, Va.). HT-1080 cells were grown in MEME (ATCC) supplemented with 10% fetal bovine serum (ATCC), and MCF7 cells were grown in the same culture medium with the addition of 0.01 mg/mL bovine insulin (Sigma-Aldrich, St. Louis, Mo.). Both cell lines were maintained in a 5% CO$_2$ incubator at 37° C. Anti-CD13 monoclonal antibody (WM15, Alexa Fluor 488-conjugated) was obtained from AbD Serotec (Raleigh, N.C.).

Cell Binding:

Cellular binding of cK(OG)NGRE to the CD13/APN marker was assessed by plating HT-1080 (CD13+) and MCF7 (CD13−) cells in eight-chambered slides (LabTekII, Nunc, Rochester, N.Y.) at a concentration of 15,000 cells/well. After 24 h, cells were washed once with phosphate-buffered saline (PBS) and incubated in complete culture media at 37° C. for 30 min with either cK(OG)NGRE (20 μM) or the anti-CD13 antibody (final concentration 2.5 μg/mL). Slides were washed twice with PBS for 5 min, fixed in 4% paraformaldehyde for 20 min, and mounted with Prolong Gold antifade reagent with DAPI (Invitrogen, Carlsbad, Calif.) and imaged with an epifluorescent microscope (Zeiss Axio Imager.M1, Thornwood, N.Y.) after 24 h.

Liposome Preparation:

Liposome was prepares as follows. DPPC:MSPC:DSPE-PEG-cNGR in molar % ratio of 86.3:9.7:5 were mixed and dissolved in chloroform and dried by solvent evaporation. The dried film was hydrated with 2.5 mL of 50 mM Calcein solution at 55° C. for an hour (10 mg lipid/mL). Then, the resulting Multilamellar preparation was sized by repeated extrusion through Nuclepore® polycarbonate membrane filters (Whatman plc, UK) with a pore size of 100 nm using LIPEX™ Extruder (Northern Lipids Inc., Burnaby, Canada) at 55° C. Particle size of the liposome was determined by dynamic light scattering spectrophotometer (ZetaPALS, Brookhaven Instruments Corporation, Holtsville, N.Y.).

Figure 7:
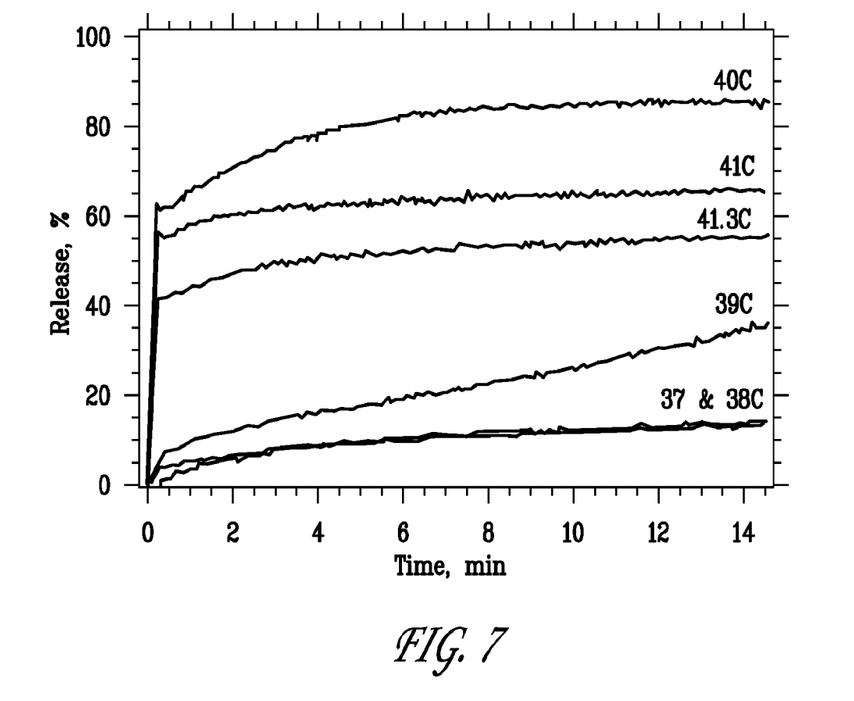
FIG. 7 shows the results of a release assay for cNGR-targeted low temperature sensitive liposomes (n=3).

Release Assay:

Release of calcein from cNGR targeted low temperature sensitive liposomes was determined using a standard release assay that measures the dequenching of calcein as it is released from the liposome. 4.0 μL of cNGR-targeted low temperature sensitive liposomes were incubated in 3 mL of plasma in a quartz cell for 15 min at a predetermined temperature. The release of calcein from cNGR-targeted low temperature sensitive liposomes was determined by fluorescence spectrophotometry (PerkinElmer, Shelton, Conn.). The excitation and emission wavelength were 492 and 520 nm, respectively. The percentage of calcein released from cNGR-targeted low temperature sensitive liposomes was calculated as follows.

$$\% \text{ release} = \frac{(F_t - F_i)}{(F_f - F_i)} \times 100$$

where:
$F_i$=initial fluorescence intensity
$F_t$=fluorescence intensity through time
$F_f$=total fluorescence intensity of the solution after the cNGR-targeted low temperature sensitive liposomes were disrupted with Triton X-100 (70 μL of 25% v/v).

Example 1

Synthesis of Cyclic cKNGRE (5) (SEQ ID NO:3)

Figure 2:
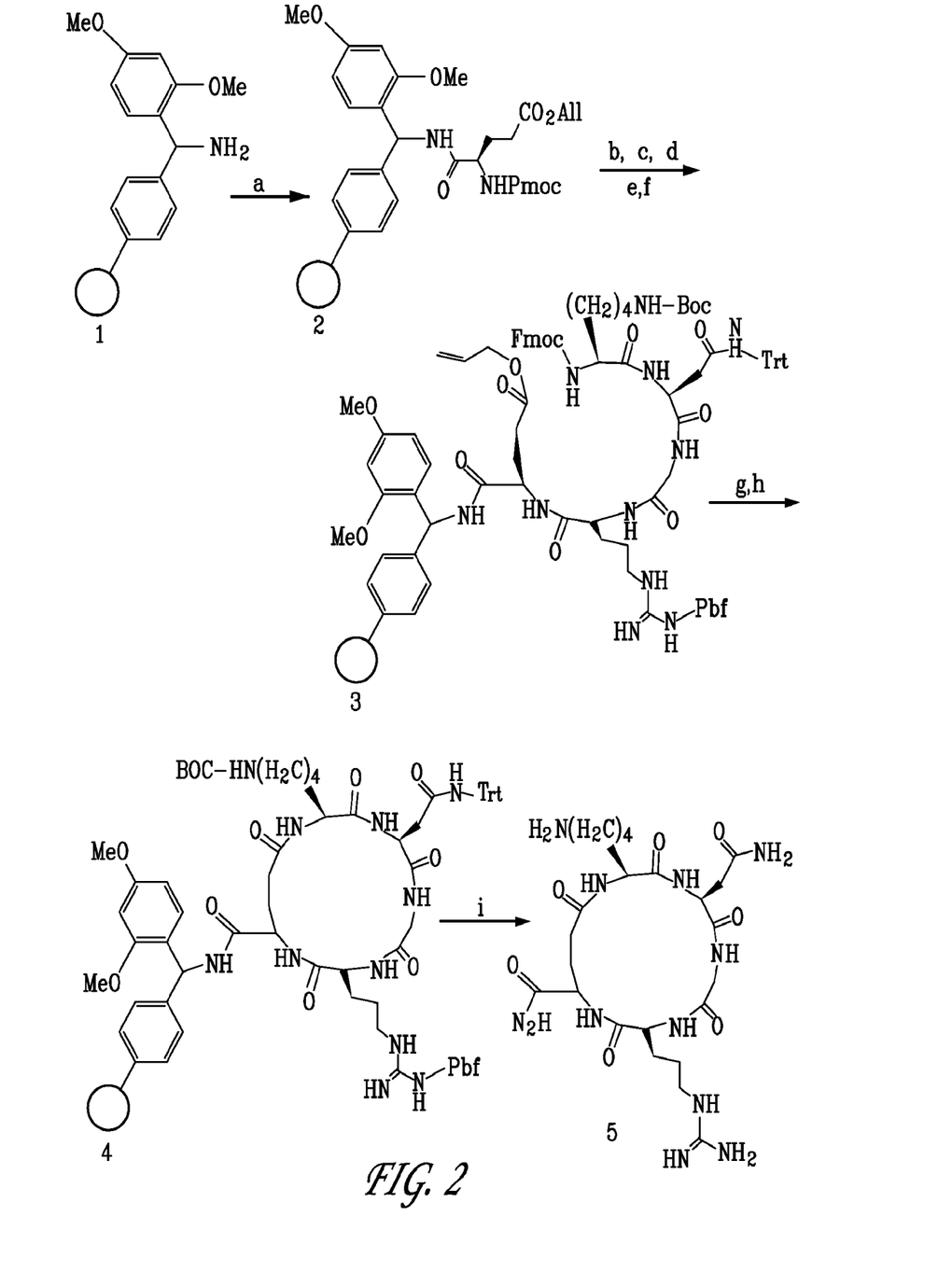

As shown in FIG. 2 NovaPEG Rink Amide Resin 1 (0.50-0.80 mmol/g loading) was washed with dichloromethane (DCM) and 1-methyl-2-pyrrolidinone (NMP), respectively, and swollen with 2 ml of DCM for 2 hours and washed with NMP prior to coupling with glutamic acid via its side chain carboxylic group, by mixing the resin with a solution of Fmoc-Glu(OAll)-OH (2.5 equivalents) and diisopropylethylamine (DIPEA) (4 equivalents) in dry NMP. The resin was capped by washing with a solution of dry CH$_2$Cl$_2$-acetic anhydride-DIPEA (20:4:1) to give compound 2. The Fmoc protecting group was removed with a solution of piperidine-NMP (1:4) and the linear pentapeptide 3 was constructed using standard Fmoc protocol by adding the respective protected amino acid (2 equivalents), 2-(1H-7-azabenzotriazol-1-yl)-1,1,3,3-tetramethyl uronium hexafluorophosphate methanaminium (HATU) (2 equivalents), and DIPEA (4 equivalents) in NMP. All Fmoc protecting groups were removed using piperidine-NMP (1:4) solution. After addition of the last amino acid, the C-terminal allyl ester was removed from 4 with Pd(PPh$_3$)$_4$ in CHCl$_3$—AcOH—N-methylmorpholine (37:2:1), under argon by occasional gentle agitation for 2 hours and washed with DIPEA-NMP (5:95) and diethyldithicarbamic acid sodium salt, respectively.

On-resin cyclization was effected by removing the N-Fmoc group from the lysine and treating with HATU (2 equivalents) and DIPEA (4 equivalents). Cleavage of the peptide from the resin and removal of all the protecting groups (2,2,4,6,7-pentamethyl-dihydrobenzofuran-5-sulfonyl (Pfb) from arginine and N-β-trityl from asparagine and N-Boc from lysine was effected by agitating the resin-peptide with TFA-DCM (1:1) for two hours and washed with trifluoroacetic acid (TFA)-dichloromethane (DCM) (1:9). The acid wash was concentrated and $Et_2O$ was added until a white precipitate separated. The precipitate was purified by reverse phase HPLC (Microsorb 100-5 C18, 250×21.4 mm id, 20-40% MeCN—$H_2O$ containing 0.1% TFA, 5 ml, 30 minute run time) and lyophilized to give the cyclic cKNGRE peptide (5) s a white powder (193 mg, 33% based on estimated loading of peptide-resin).

Example 2

Synthesis of Cyclic cK(OG)NGRE (6) (SEQ ID NO:2)

Figure 3:
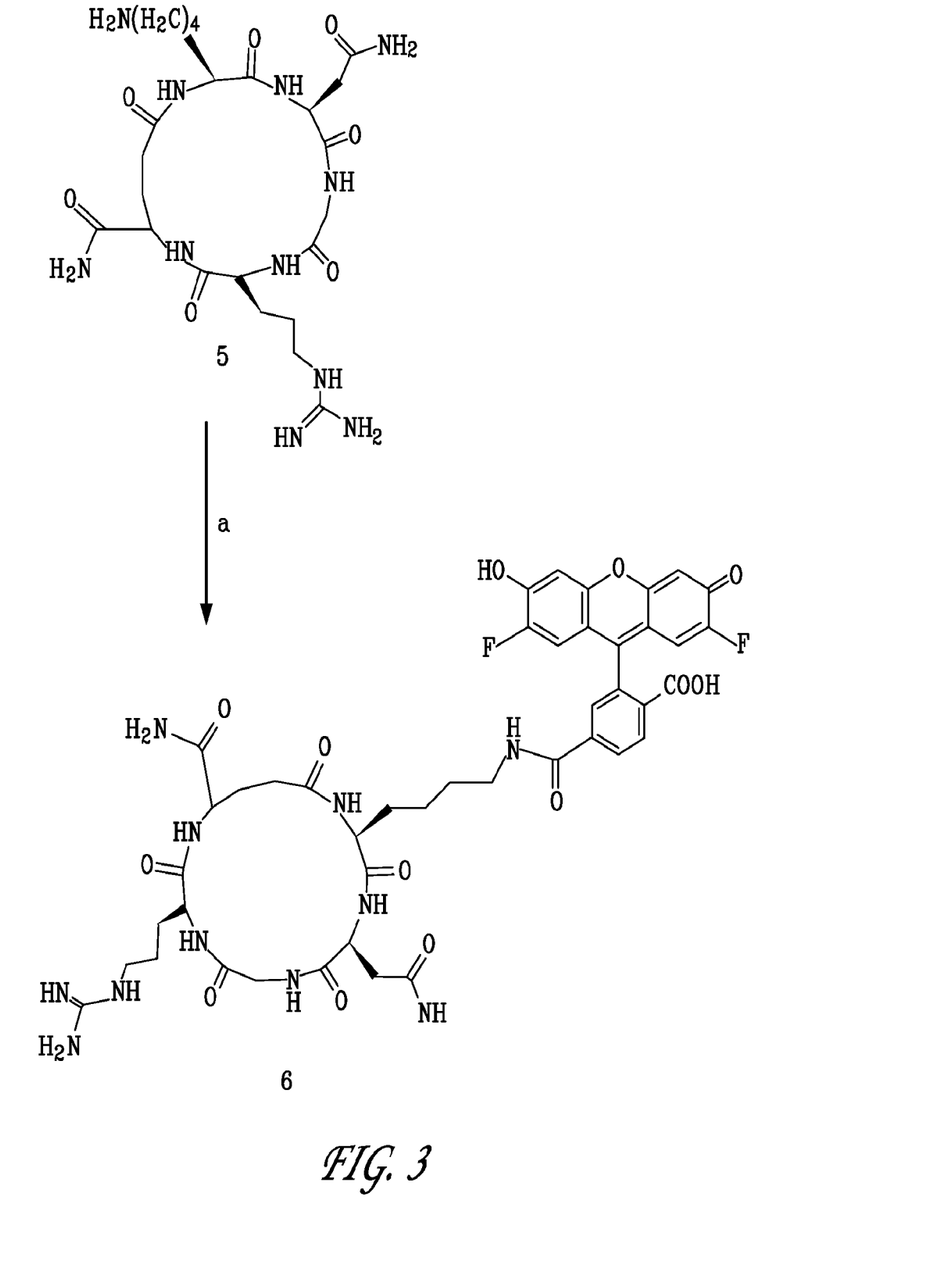
FIG. 3 shows a synthetic scheme for producing the compound of EXAMPLE 2.

As shown in FIG. 3 to a solution of the compound prepared in Example 1 (5.2 mg, 0.0089 mmol) and Oregon Green 488 carboxylic acid, succinimidyl ester, 6-isomer (5 mg, 0.0098 mmol) in NMP (1 ml), DIPEA (3 μl) was added and the resulting reaction mixture was stirred for 5 hours at room temperature. The reaction mixture was precipitated by pouring into 20 mL of diethylether, filtered and washed with diethylether. The resulting precipitate was dissolved in water and purified with reverse phase-HPLC (Microsorb 100-5 C18, 250×21.4 mm id, 20-40% MeCN—$H_2O$ containing 0.1% TFA, 5 ml, 30 minute run time) and lyophilized to give peptide-dye conjugate, cyclic cK(OG)NGRE, 6 as a yellow powder (6.3 mg, 72%).

Example 3

Synthesis of DSPE-PEG-cNGR Conjugate (7)

Figure 4:
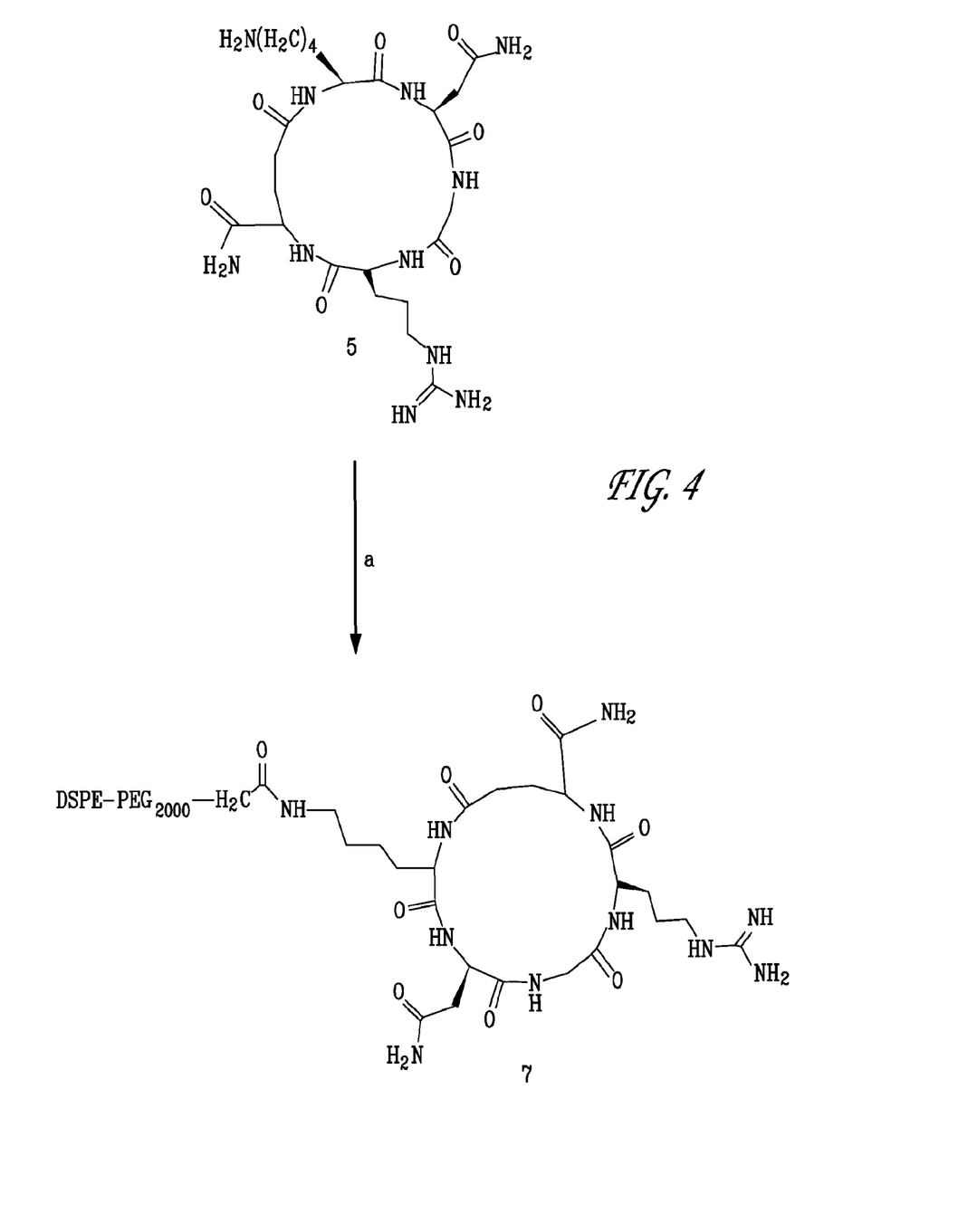
FIG. 4 shows a synthetic scheme for producing the composition of EXAMPLE 3.

As shown in FIG. 4 to a solution of DSPE-$PEG_{2000}CH_2COOH$ (50 mg, 0.018 mmol) and dicyclohexylcarbo-diimide (DCC) (4.4 mg, 0.021 mmol) and N-hydroxybenzotriazole (HOBt) (2.8 mg. 0.021 mmol) in NMP (1 ml), DIPEA (3 μl) was added and the resulting reaction mixture was stirred for 30 minutes at ambient temperature and the compound prepared in Example 1 (12.3 mg, 0.21) was added and the resulting reaction mixture was allowed to stir overnight at ambient temperature. The resulting reaction mixture was precipitated by pouring into diethylether (20 mL) and the precipitate wash washed with diethylether and gently blown with argon to remove the solvent. The resulting powder was dissolved in MeOH:$CHCl_3$ (1:2) and purified with Sephadex-LH20 ($CHCl_3$:MeOH 2:1) to give DSPE-PEG-cNGR conjugate (7) as a transparent solid (40 mg, 65%).

Example 4

Visualization of cK(OG)NGRE Binding to CD13 Positive Cells

Figure 5A:
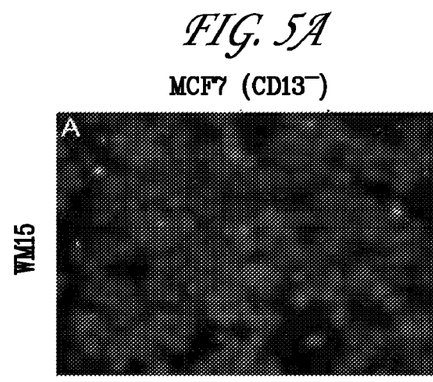

To evaluate in vitro binding of the cKNGRE to human carcinoma cells, cKNGRE was conjugated to the fluorophore Oregon Green (cK(OG)NGRE) (SEQ ID NO:2) for visualization via epifluorescent microscopy. cK(OG)NGRE and the anti-CD13 antibody WM15 were incubated with HT-1080 (CD13+) and MCF7 (CD13−) cells. Green signal indicates cK(OG)NGRE (SEQ ID NO:2) or anti-CD13 antibody and blue signal indicates the nuclear staining agent, DAPI. cK(OG)NGRE (SEQ ID NO:2) and WM15 clearly demonstrated binding to HT-1080 cells (FIG. 5B AND FIG. 5E), whereas these agents displayed minimal binding to MCF7 cells (FIG. 5A AND FIG. 5D). Antibody fluorescence was membrane-associated and dispersed across the cell surface. In addition to membrane fluorescence, intense punctuate fluorescence was observed in HT-1080 cells incubated with cK(OG)NGRE (SEQ ID NO:2) (FIG. 5E), indicating internalization of the peptide. At higher magnification (FIG. 5C, FIG. 5F), the membrane localization of cK(OG)NGRE (SEQ ID NO:2) and WM15 appeared identical with the exception of the bright punctuate signal associated with the NGR-OG agent.

In summary, FIGS. 5A to 5F show fluorescence micrographs of in vitro binding of anti-CD13 antibody (FIGS. 5A, 5B, and 5C) and cK(OG)NGRE (SEQ ID NO:2) (FIGS. 5D, E, and F) to CD13-positive HT-1080 cells (FIGS. 5B, C, E, and F) and CD13-negative MCF7 cells (FIGS. 5A and D), where:

green is a signal from cK(OG)NGRE (SEQ ID NO:2) or anti-CD13 antibody; and blue is signal from the nuclear staining agent DAPI.

Figures 5A, 5B, 5C, 5E, 5F:
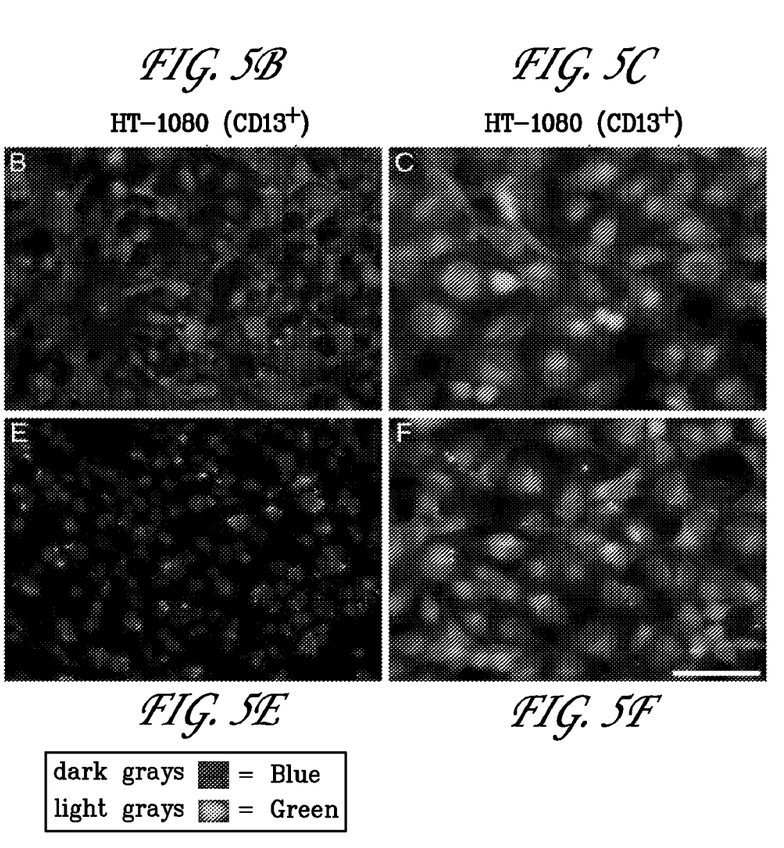
Figure 5D:
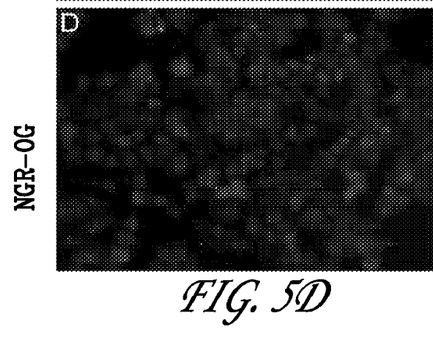

Bar equals 100 μM for FIGS. 5A, B, D, and E and 50 μM for FIGS. 5C and F.

Example 5

Figure 6A:
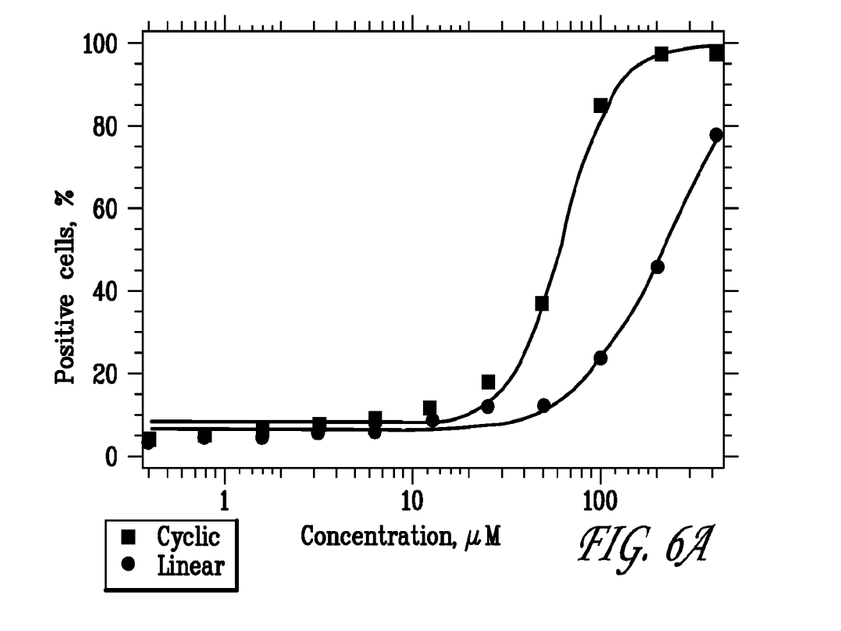
FIG. 6A and FIG. 6B show the half maximal effective concentration ($EC_{50}$) plots for binding to CD13-positive HT-1080 cells for free cyclic and linear NGR peptide (FIG. 6A) as well as targeted low temperature sensitive liposomes (FIG. 6B).
Figure 6B:
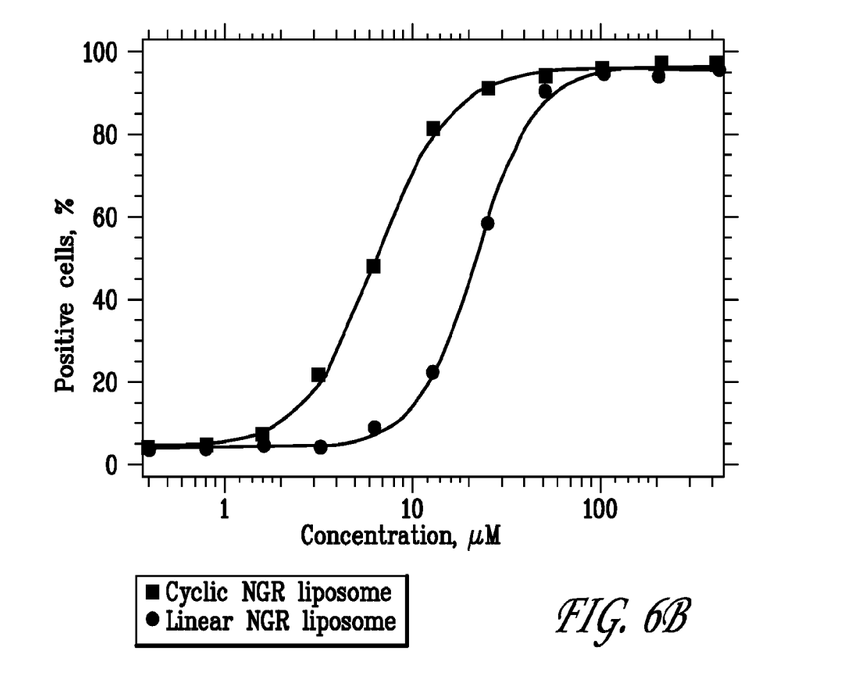

Binding of cK(OG)NGRE (SEQ ID NO:2) and Low Temperature Sensitive Liposomes with 5 mol % DSPE-PEG-cNGR to CD13 Positive Cells To determine the half maximal effective concentration ($EC_{50}$) of cK(OG)NGRE (SEQ ID NO:2) and low temperature sensitive liposomes targeted with 5 mol % DSPE-PEG-cNGR, flow cytometry was performed according to standard procedures with HT-1080 cells. Approximately 94% of the HT-1080 cells were positive for the WM15 antibody indicating the presence of CD13 on these cells. As shown in FIG. 6A, the cyclic peptide, cK(OG)NGRE (SEQ ID NO:2) ($EC_{50}$=61.0 μM), binds to HT-1080 cells at a lower concentration than a linear form of an NGR-containing peptide (SEQ ID NO:4) ($EC_{50}$=219.9 μM). Low temperature sensitive liposomes targeted with a cyclic peptide ($EC_{50}$=6.2 μM) bind at a concentration 3.5-fold lower than a liposome with a linear peptide ($EC_{50}$=21.5 μM) as shown in FIG. 6B. These data demonstrate that the cyclic cK(OG)NGRE (SEQ ID NO:2) performs better than a linear NGR peptide and their binding constants are sufficient for biological applications.

In summary, FIG. 6A and FIG. 6B show the half maximal effective concentration ($EC_{50}$) plots for binding to CD13-positive HT-1080 cells for free cyclic and linear NGR peptide (FIG. 6A) as well as targeted low temperature sensitive liposomes (FIG. 6B).

Example 6

Release of Calcein from Low Temperature Sensitive Liposomes with 5 mol % DSPE-PEG-cNGR cNGR-targeted low temperature sensitive liposomes were 100.2±1.6 nm in diameter. The release of calcein from a cNGR-targeted low temperature sensitive liposome in plasma is shown in FIG. 7 (n=3). There was very little release of calcein at 37 and 38° C. This release increased substantially with increasing temperature up to 40° C. where about 84% is released after 14 minutes. More importantly, 62% is released within 15 seconds of heating at 40° C. These data suggest that cNGR-targeted low temperature sensitive liposomes may be used with regional hyperthermia in vivo to improve drug delivery.

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I (SEQ ID NO:1):

I or a pharmaceutically-acceptable salt thereof;
wherein:

$R^1$ is $(CH_2)_4NR^{12}R^{14}$;

$R^2$ is hydrogen or $C_1$-$C_6$alkyl;

$R^3$ is $CH_2C(=O)NR^{12}R^{15}$;

$R^4$ is hydrogen or $C_1$-$C_6$alkyl;

$R^5$ is hydrogen or $C_1$-$C_6$alkyl;

$R^6$ is hydrogen or $C_1$-$C_6$alkyl;

$R^7$ is $(CH_2)_3NHC(NR^{12}R^{14})(=N^+R^{12}R^{16})$;

$R^8$ is hydrogen or $C_1$-$C_6$alkyl;

$R^9$ is hydrogen or $C_1$-$C_6$alkyl;

$R^{10}$ is hydrogen or $C_1$-$C_6$alkyl;

$R^{11}$ is hydrogen or $C_1$-$C_6$alkyl;

each $R^{12}$ is, independently, hydrogen or $C_1$-$C_6$alkyl;

$R^{13}$ is hydrogen, $C_1$-$C_6$alkyl, or -(L)$_n$-sm;

L is a linking moiety;

n is 0 or 1;

sm is a support medium;

$R^{14}$ is hydrogen, $C_1$-$C_6$alkyl, amino protecting group, or a diagnostic moiety that is a fluorophore, a non-metallic isotope, an optical reporter, a boron neutron absorber, a paramagnetic metal ion, a ferromagnetic metal, a gamma-emitting radioisotope, a positron-emitting radioisotope, or an x-ray absorber;

$R^{15}$ is hydrogen, $C_1$-$C_6$alkyl, or amino protecting group; and $R^{16}$ is hydrogen, $C_1$-$C_6$alkyl, or a guanidino-protecting group.

2. A compound of claim 1, wherein $R^1$ is $(CH_2)_4NH_2$.

3. A compound of claim 1, wherein $R^2$ is hydrogen.

4. A compound of claim 1, wherein $R^3$ is $CH_2C(=O)NH_2$.

5. A compound of claim 1, wherein $R^4$ is hydrogen.

6. A compound of claim 1, wherein $R^5$ is hydrogen.

7. A compound of claim 1, wherein $R^6$ is hydrogen.

8. A compound of claim 1, wherein $R^7$ is $(CH_2)_3NHC(NH_2)(=N^+H_2)$.

9. A compound of claim 1, wherein $R^8$ is hydrogen.

10. A compound of claim 1, wherein $R^9$ is hydrogen.

11. A compound of claim 1, wherein $R^{10}$ is hydrogen.

12. A compound of claim 1, wherein $R^{11}$ is hydrogen.

13. A compound of claim 1, wherein $R^{12}$ is hydrogen.

14. A compound of claim 1, wherein $R^{13}$ is hydrogen.

15. A compound of claim 1, herein $R^{13}$ is -(L)$_n$-sm.

16. A compound of claim 1, wherein:
L is

17. A compound of claim 1, wherein n is 0.
18. A compound of claim 1, wherein n is 1.
19. A compound of claim 1, wherein $R^{14}$ is hydrogen.
20. A compound of claim 1, wherein $R^{14}$ is a diagnostic moiety.
21. A compound of claim 20, wherein said diagnostic moiety is a fluorophore.
22. A compound of claim 21, wherein said fluorophore is 23. A compound of claim 1, wherein $R^{14}$ is an amino protecting group.
24. A compound of claim 23, wherein said amino protecting group is t-butyloxy carbonyl (BOC).
25. A compound of claim 1, wherein $R^{15}$ is hydrogen.

26. A compound of claim 1, wherein $R^{15}$ is an amino protecting group.
27. A compound of claim 26, wherein said amino protecting group is triphenylmethyl (trityl).
28. A compound of claim 1, wherein $R^{16}$ is hydrogen.
29. A composition, comprising:
   a compound of claim 1 or a pharmaceutically acceptable salt thereof;
   a lipid-bilayer;
   at least one diagnostic agent that is a fluorophore, a non-metallic isotope, an optical reporter, a boron neutron absorber, a paramagnetic metal ion, a ferromagnetic metal, a gamma-emitting radioisotope, a positron-emitting radioisotope, or an x-ray absorber;
   or at least one therapeutic agent that is an anti-tumor agent, an anti-angiogenic agent, anti-neoplastic agent, or a combination thereof; and
   optional polyethylene glycol.
30. A composition of claim 29, wherein said lipid-bilayer comprises liposomes.
31. A composition of claim 29, wherein said therapeutic agent is an anthracycline compound.
32. A composition of claim 29, wherein said compound of claim 1 or said pharmaceutically acceptable salt thereof is conjugated to said lipid bilayer.
33. A method of imaging cancerous tissue in a patient comprising:
   administering to said patient a composition of claim 29 comprising at least one diagnostic agent; wherein said cancerous tissue expresses aminopeptidase N isoform CD13 (APN/CD13); and
   performing imaging on the patient to detect the composition bound to the cancerous tissue.
34. The compound of claim 1, wherein the guanidino-protecting group is 5-sulfonyl-2,2,4,6,7-pentamethyl-benzofuran.
35. A method of treating cancer in a patient comprising
   administering to said patient a composition of claim 29 comprising the least one therapeutic agent; wherein said cancerous tissue expresses aminopeptidase N isoform CD13 (APN/CD13).
36. The composition of claim 30, wherein the liposomes are sensitive at 39 degrees Celsius to 41 degrees Celsius.

* * * * *

UNITED STATES PATENT AND TRADEMARK OFFICE
CERTIFICATE OF CORRECTION

PATENT NO. : 8,636,978 B2  Page 1 of 1
APPLICATION NO. : 13/000543
DATED : January 28, 2014
INVENTOR(S) : Wood et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 474 days.

Signed and Sealed this
Twenty-second Day of September, 2015

Michelle K. Lee
*Director of the United States Patent and Trademark Office*